(12) United States Patent
Shaw et al.

(10) Patent No.: US 9,138,545 B2
(45) Date of Patent: Sep. 22, 2015

(54) NEEDLE RETRACTION APPARATUS

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Leonard, TX (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 133 days.

(21) Appl. No.: 13/714,819

(22) Filed: Dec. 14, 2012

(65) Prior Publication Data

US 2014/0171830 A1 Jun. 19, 2014

(51) Int. Cl.
| | |
|---|---|
| *A61B 5/00* | (2006.01) |
| *A61M 5/32* | (2006.01) |
| *A61B 5/15* | (2006.01) |
| *A61B 5/153* | (2006.01) |

(52) U.S. Cl.
CPC ............ *A61M 5/3232* (2013.01); *A61B 5/1405* (2013.01); *A61B 5/1535* (2013.01); *A61B 5/150885* (2013.01); *A61B 5/15003* (2013.01); *A61B 5/150389* (2013.01); *A61B 5/150503* (2013.01); *A61B 5/150732* (2013.01); *A61M 5/3202* (2013.01); *A61M 2005/3227* (2013.01)

(58) Field of Classification Search
CPC . A61B 5/1405; A61B 5/1438; A61B 5/15003
USPC .................................. 600/573, 576
See application file for complete search history.

(56) References Cited

U.S. PATENT DOCUMENTS

| | | | | |
|---|---|---|---|---|
| 4,747,831 | A * | 5/1988 | Kulli ............................ | 604/110 |
| 5,395,337 | A * | 3/1995 | Clemens et al. ............. | 604/110 |
| 2001/0021827 | A1* | 9/2001 | Ferguson et al. ............. | 604/198 |
| 2004/0015135 | A1* | 1/2004 | Wilkinson .................... | 604/192 |
| 2004/0133172 | A1* | 7/2004 | Wilkinson .................... | 604/263 |
| 2005/0004524 | A1* | 1/2005 | Newby et al. ........... | 604/164.08 |
| 2006/0155244 | A1 | 7/2006 | Popov | |
| 2006/0189934 | A1* | 8/2006 | Kuracina et al. ............. | 604/110 |
| 2007/0260189 | A1* | 11/2007 | Shaw et al. .................. | 604/187 |
| 2008/0132851 | A1* | 6/2008 | Shaw et al. .................. | 604/199 |
| 2008/0319345 | A1* | 12/2008 | Swenson ...................... | 600/576 |
| 2009/0198196 | A1* | 8/2009 | West et al. .................... | 604/263 |
| 2009/0306601 | A1* | 12/2009 | Shaw et al. .................. | 604/177 |
| 2010/0000040 | A1* | 1/2010 | Shaw et al. .................. | 15/244.1 |
| 2010/0003067 | A1* | 1/2010 | Shaw et al. .................. | 401/206 |
| 2010/0286604 | A1* | 11/2010 | Shaw ............................ | 604/68 |
| 2012/0071790 | A1* | 3/2012 | Mahurkar .................... | 600/577 |
| 2012/0259243 | A1* | 10/2012 | Shaw et al. .................. | 600/576 |

* cited by examiner

*Primary Examiner* — Sean Dougherty
*Assistant Examiner* — Daniel Cerioni
(74) *Attorney, Agent, or Firm* — Ross Barnes LLP; Monty L. Ross; Robin L. Barnes (57) ABSTRACT

A needle retraction apparatus for a medical device such as a liquid infusion or collection device, the apparatus having a body, a needle retraction mechanism seated inside the body, a transverse slide member with an external needle retraction chamber, and a retraction actuator that is rotatable relative to the slide member, the retraction actuator being attachable to or made as part of the liquid infusion or collection device, whereby rotation of the device causes the slide member to move in a linear translational direction to reposition the retraction chamber in alignment with the needle retraction mechanism and allow retraction.

28 Claims, 7 Drawing Sheets

NEEDLE RETRACTION APPARATUS

BACKGROUND OF THE INVENTION

1. Field of the Invention

This invention relates to a needle retraction apparatus for medical devices. One aspect of the invention relates to a new needle retraction apparatus that can be attached to or manufactured together with, or as an integral part of, a medical device such as a syringe, catheter, or other liquid infusion or collection device. Another aspect of the invention relates to a needle retraction apparatus that is rotationally activated and cam operated. Another aspect of the invention relates to a needle retraction apparatus for a liquid infusion or collection device, the apparatus having a body with a forwardly facing, rearwardly biased needle, in which needle retraction is initiated by manually rotating an actuator to interrupt a fluid flow path through the apparatus and reposition a needle retraction chamber. Another aspect of the invention relates to a frontal attachment for a liquid infusion or collection device that comprises a tubular retraction chamber external to any cavity of the device, which retraction chamber is repositioned by linear translational movement into alignment with a rearwardly biased needle holder. Another aspect of the invention relates to a needle retraction apparatus for a medical device such as, for example, a glass or plastic syringe, having a luer lock or other similarly effective connector and comprising a needle retraction chamber that is external to the syringe. Another aspect of the invention relates to a method for retracting a needle in a medical device whereby rotating an actuator and cam causes a needle retraction chamber to be repositioned into alignment with a rearwardly biased needle by linear translational movement.

2. Description of Related Art

Conventional syringes comprising a generally cylindrical barrel, a fixed needle projecting forwardly from the barrel, and a plunger slidably disposed inside the barrel through an opening in the rear of the barrel are well known. More recently, syringes have been made with a luer connector on the front of the barrel to which a needle hub is attachable to allow needles of different gauges or sizes to be used with a commonly configured barrel.

Even more recently, in an effort to control the spread of blood-borne pathogens and the incidence of contamination by contact with either exposed needles or bodily fluids, syringes having fixed or changeable needles have been designed to embody various "safety" elements. Such "safety" elements should desirably include a retractable needle, but many products marketed as having "safety" elements include, for example, covers or guards that are manually operated by medical personnel administering an injection to shield or cover the needle tip following removal of the needle from a patient.

Some previously disclosed needle retraction systems without changeable needles are activated either manually or automatically by application of a force upon completion of an injection to force the needle and needle tip back inside a retraction chamber. The only known syringe having a changeable, retractable needle does not have a conventional luer lock connection, and the retraction mechanism is activated by the application of a forwardly directed force to the plunger handle following removal of the needle from a patient, thereby exposing the needle and also exposing the user to the risk of needle-stick injury.

U.S. Publ. No. 2006/0155244 to Popov discloses a venipuncture device that rotates a port unit following needle retraction. The retraction chamber is disposed inside the medical device, is not part of the frontal attachment and remains stable while the port unit is moved rotationally relative to the retraction chamber following needle retraction. The frontal attachment disclosed there cannot be used with a generic luer lock syringe.

Although many advancements in syringe technology have been made in recent years, a frontal attachment is needed that can be used with a standard syringe having a conventional luer lock connector, that has a needle retraction chamber external to the syringe with which the frontal attachment is used, that offers the advantages of a retractable needle having sufficient retraction force to retract the needle while inserted into a patient, and that can be activated by the application of a rotational force to the syringe barrel, thereby moving the external retraction cavity into alignment with a rearwardly biased needle without applying a forwardly directed force to the plunger or the needle.

SUMMARY OF THE INVENTION

A needle retraction apparatus having a retractable needle is disclosed for use with a medical device such as a liquid infusion or collection device. For example, the needle retraction apparatus of the invention can be used with a conventional glass or plastic syringe, either prefilled or not, having a conventional luer lock connector, threaded connector, snap connector, tubular connector, bayonet style connector or other similarly effective connector known to those of skill in the art for providing a substantially fluid-tight liquid flow path between the needle retraction apparatus and the liquid infusion or collection device. The liquid infusion or collection device is not limited to syringes, and can for example be configured as an IV-catheter introducer or blood collection set. The needle retraction apparatus can also be configured as a frontal attachment, and can have a proprietary connector if desired to limit its use to particular medical devices made by particular manufacturer. Alternatively, the subject needle retraction apparatus can be made to be fully functional with any medical device having a cooperatively configured connector, or can be integrally formed with or assembled to another device during manufacture so as to provide a single unit to the user.

Where the needle retraction apparatus of the invention is a syringe, the apparatus is desirably configured so that needle retraction is initiated by rotating the syringe barrel following injection rather than by advancing the plunger handle relative to the barrel. This ability to initiate needle retraction without applying any additional forwardly directed force to the plunger handle or the patient is viewed as another distinction between this and prior art devices. Prior to an injection, the central longitudinal axis of the syringe is coaxially aligned with the longitudinal axis of the needle that projects forwardly from the body of the apparatus. A retraction chamber that is part of the needle retraction apparatus and is not part of the syringe is disposed externally to the syringe, preferably in closely spaced, substantially parallel alignment to the longitudinal axis of the syringe. Following an injection, the syringe barrel is rotated relative to the body of the needle retraction apparatus to initiate needle retraction, and a cam that is also part of the frontal attachment causes the retraction chamber to be repositioned by linear translational movement to a retraction position wherein the longitudinal axis of the retraction chamber is substantially aligned with the longitudinal axis of the needle. When this occurs, a biasing force that is exerted on the needle holder by a compressed spring seated inside the body of the apparatus causes the needle holder and at least part of the needle to move into the retraction chamber to a point where the needle tip no longer projects forwardly from the body, thereby rendering the device "safe" against accidental needle sticks and effectively preventing reuse of the needle retraction apparatus.

One of many possible characterizations of the needle retraction apparatus of the invention is, a frontal attachment for a syringe having a luer lock connector, the frontal attachment comprising a body with a forwardly projecting retractable needle, a slide member mounted transversely to the needle and comprising a rearwardly projecting tubular needle retraction chamber external to the syringe, a rotatable actuator attachable to the slide member that can selectively reposition the needle retraction chamber into substantial alignment with the retractable needle to permit needle retraction following an injection, and a needle retraction assembly primarily disposed inside of and between a nose portion of the body and a fluid seal disposed in a recess in the forwardly facing surface of the actuator. A removable needle cover is also desirably provided as part of the frontal attachment to protect the needle from contamination prior to an injection. The actuator desirably further comprises a rear opening defining the rear end of a tapered luer receptacle that is frictionally engageable with a forwardly extending luer tip of a syringe, and a pair of radially projecting tabs are disposed on opposite side of the rear opening to engage female threads inside the collar portion of a luer lock connector at the front end of a conventional syringe. The actuator has an interior flow path that provides fluid communication through the actuator as part of a longer fluid flow path from the syringe to the needle. The end of the actuator disposed opposite the luer receptacle desirably comprises a cam that pushes against the body and imparts linear translational movement to the slide member when the syringe is rotated around its longitudinal axis while stabilizing the body. When the cam has repositioned the slide member sufficiently that the retraction chamber is disposed in substantially coaxial alignment with the needle retraction mechanism, the needle retraction assembly will bias the needle into the retraction chamber a sufficient distance that the needle tip no longer projects forwardly from the body.

Although a needle retraction apparatus as disclosed here is preferentially configured to be attachable to the front of a syringe having a conventional luer lock connector, it will be appreciated by those of ordinary skill in the art upon reading this disclosure that, if desired, the apparatus of the invention can be made using other connectors. For example, a snap-on or other attachment mechanism can be used instead of a conventional luer lock connector, provided that the syringe with which it is used is cooperatively configured, that fluid leakage is avoided, and that rotation of the syringe barrel is effective to rotate the actuator and thereby reposition the slide member and retraction chamber to the retraction position.

Another characterization of the invention is a needle retraction apparatus comprising a body, slide member with a needle retraction chamber, rotatable actuator, retractable needle assembly, and removable needle cap. The removable needle cap further comprises a member that is releasably engageable with cooperating parts of the body, slide member and actuator to prevent accidental rotation of the actuator and needle retraction prior to use. The retractable needle assembly preferably further comprises a needle, needle holder, retraction spring and fluid seal. A continuous fluid flow path is desirably provided through the needle, needle holder, fluid seal and rotatable actuator to establish fluid communication through the needle retraction apparatus prior to injection.

Another characterization of the invention is a method for achieving needle retraction in a syringe having a frontal attachment, whereby needle retraction is initiated by rotational movement of a cam that produces linear translational movement of a slide member comprising a retraction chamber to reposition and align the retraction chamber with a rearwardly biased needle that is thereby released into the retraction chamber.

A needle retraction apparatus as disclosed herein desirably comprises a retraction chamber that is external to the syringe or plunger handle and has sufficient retraction force to retract a needle that is still inserted into a patient's body, thereby preventing exposure of the contaminated needle or bodily fluids carried on or in the needle to others. Where the needle retraction apparatus is used with a syringe, a clinician administering an injection desirably rotates the syringe barrel in either direction relative to the body of the apparatus. As the body of the apparatus is stabilized by one hand of the user, the syringe barrel is rotated relative to the body, which first causes the slide member to move laterally out of coaxial alignment with the needle holder and needle, and then to move the retraction chamber into substantial coaxial alignment with the head of the needle holder, allowing the needle holder to carry the attached needle rearwardly to a fully retracted position where the needle is released from the patient and the needle tip no longer projects forwardly from the body of the attachment device.

BRIEF DESCRIPTION OF THE DRAWINGS

An illustrative embodiment of the needle retraction apparatus of the invention is further described and explained in relation to the following drawings wherein.

DESCRIPTION OF THE PREFERRED EMBODIMENTS

Figure 1:
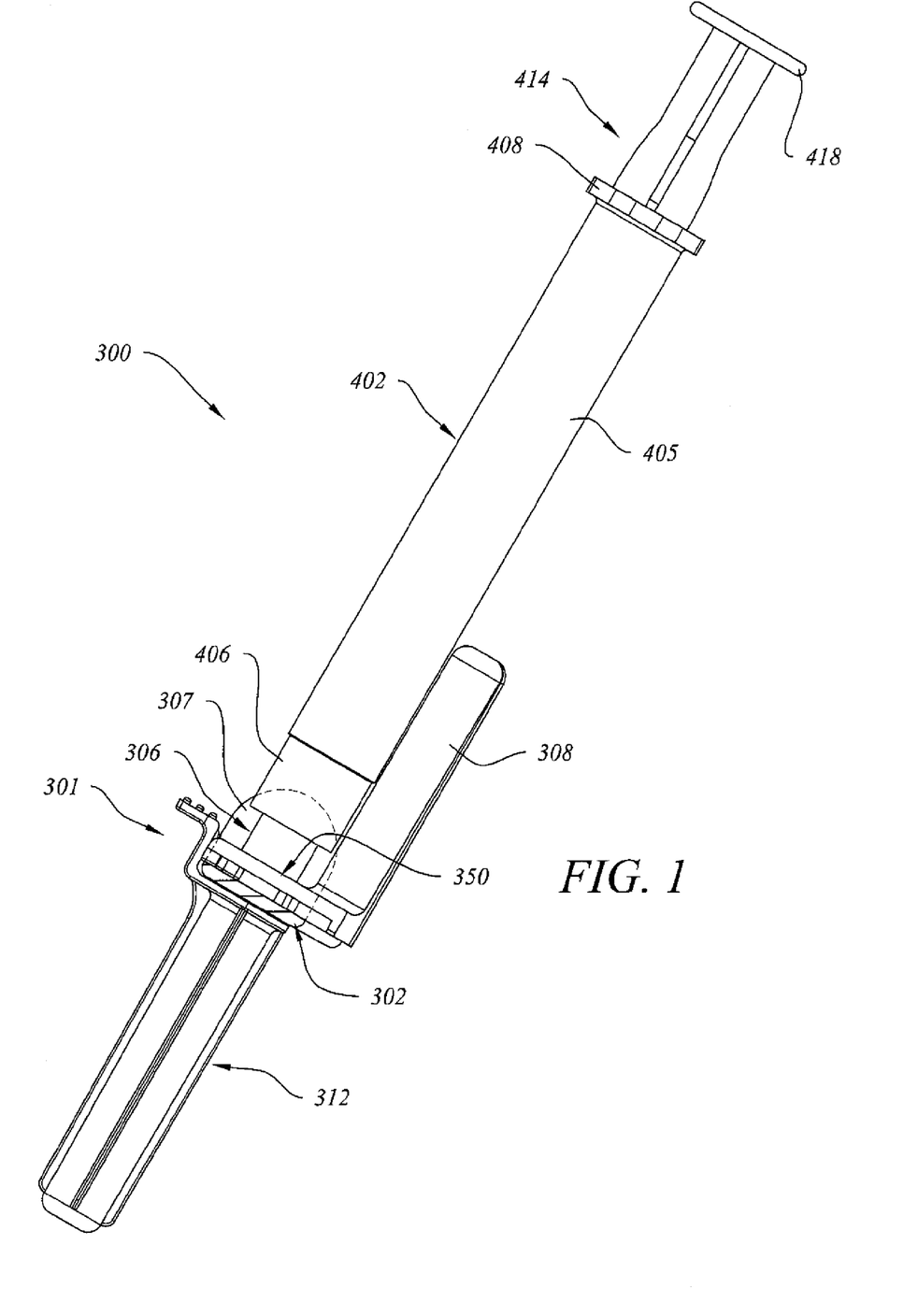
FIG. 1 is a front elevation view (inclined to fit the page), partially in cross-section, of one embodiment of a syringe having selectively attached to its front end one embodiment of a frontal attachment of the invention in the pre-use position with a portion of the body, with the section being taken behind rearwardly projecting wall member 304 (see FIG. 2) of the body to reveal the connection between the frontal attachment and a syringe having a luer lock connector.

FIG. 1 depicts an assembled combination 300 comprising frontal attachment 301, which is one embodiment of the needle retraction apparatus of the invention, attached to a conventional syringe 402. Syringe 402 is desirably a conventional syringe having a luer lock connector 406. As such, syringe 402 can typically further comprise diametrically opposed finger grips 408, 410 at or near the rear of barrel 405, and a plunger assembly 414 that further comprises plunger handle 416 with thumb cap 418, plunger seal attachment boss 420, and plunger seal 422 that slidably engages the interior wall of barrel 405.

Frontal attachment 301 desirably comprises body 302, actuator 306, slide member 350, a forwardly projecting needle and needle retraction assembly (not visible in FIG. 1), and removable needle cover 312. Actuator 306 is rotatably mounted in slide member 350, which desirably further comprises rearwardly projecting tubular needle retraction chamber 308. In FIG. 1, in order to better illustrate the connection between actuator 306 and luer lock connector 406, a cross-section is taken through the front wall of body 302 to prevent wall 304 (visible in FIGS. 2 and 3) from obscuring the attachment of frontal attachment 301 to syringe barrel 402.

Figure 2:
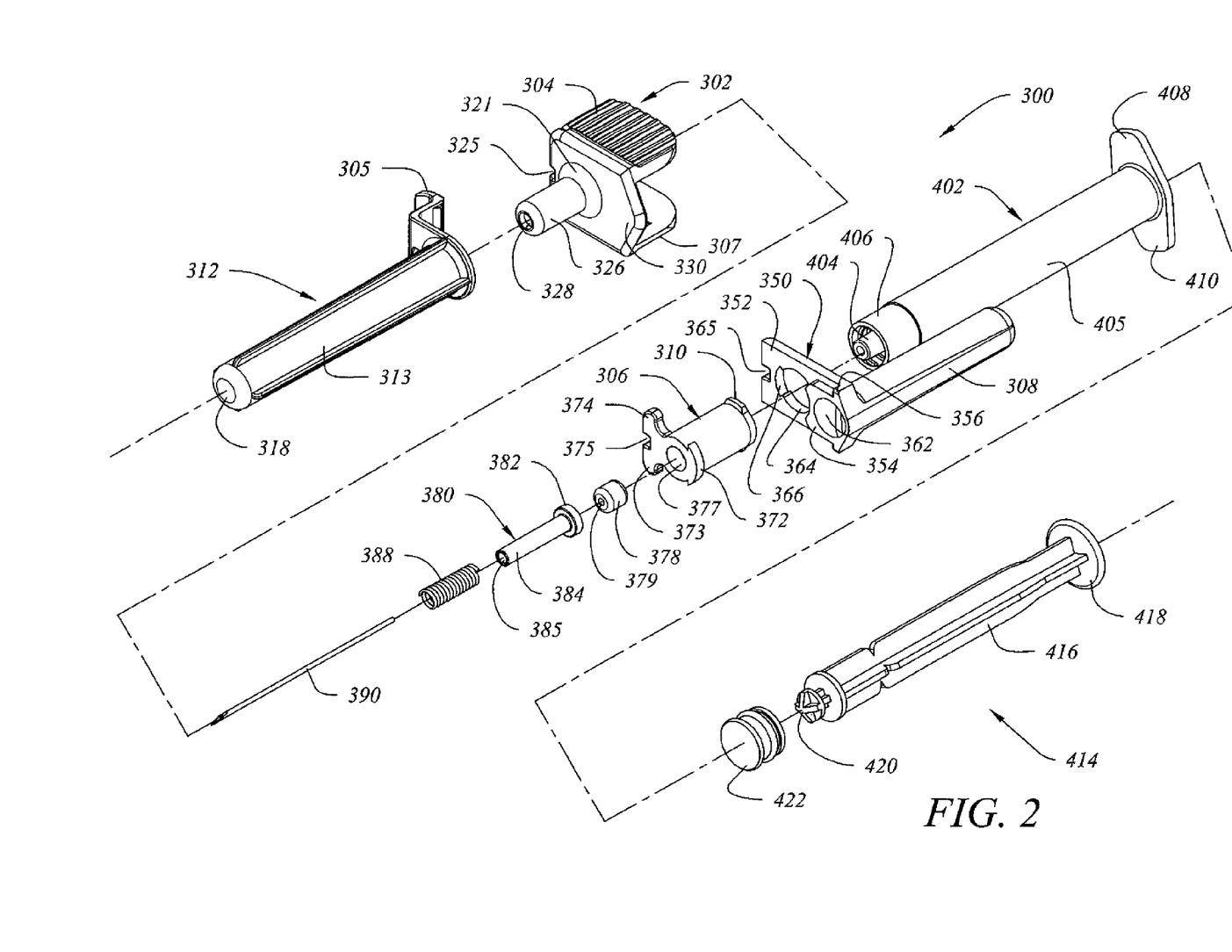
FIG. 2 is an exploded front perspective view of the combination of FIG. 1.
Figure 3:
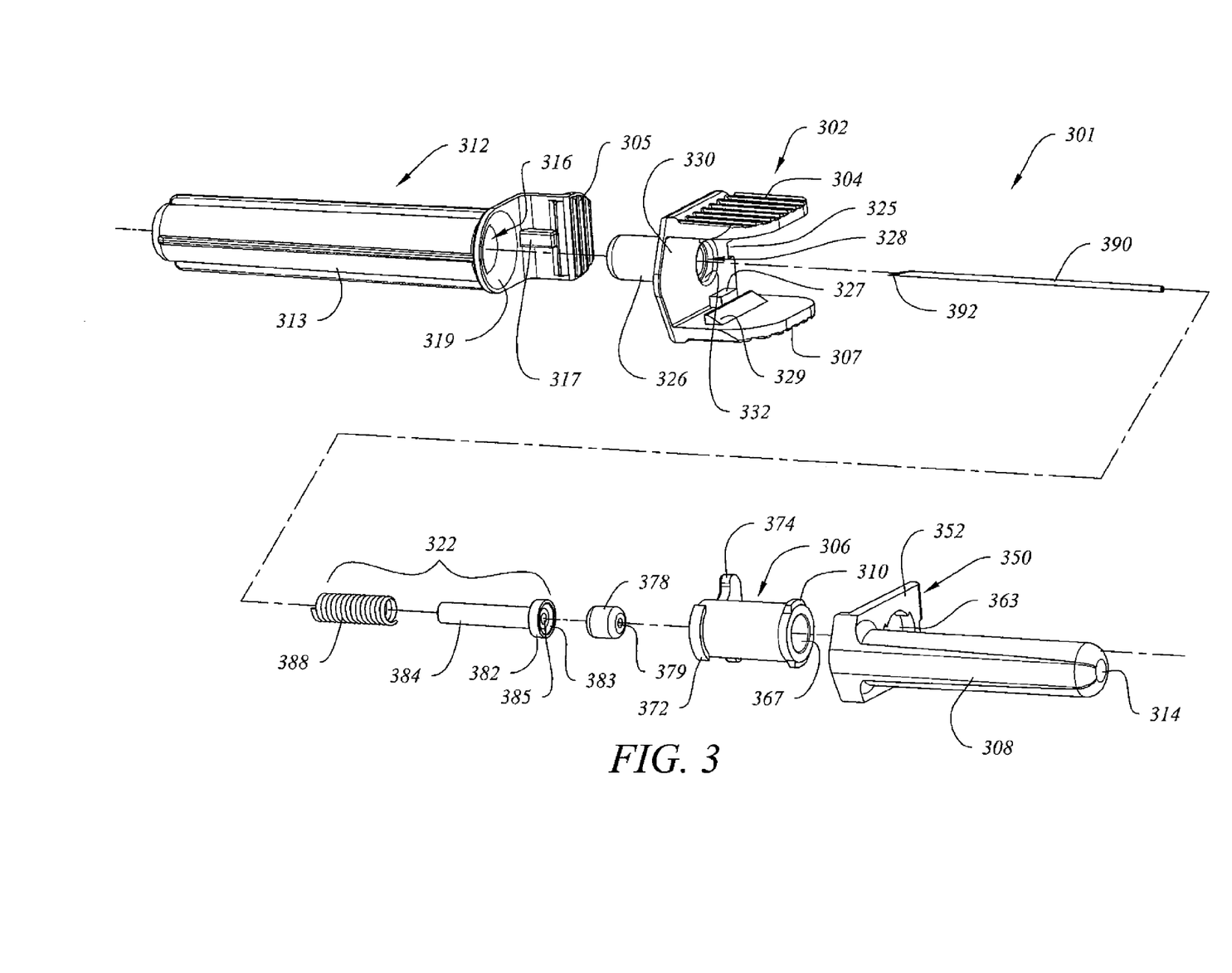
FIG. 3 is an exploded rear perspective view of the frontal attachment portion of FIG. 1.

FIG. 2 depicts the component parts of this embodiment of combination 300 and frontal attachment 301 in an exploded layout from a front perspective, and FIG. 3 depicts an enlargement of the frontal attachment 301 portion of FIG. 2 from a rear perspective so as to better illustrate and describe the invention. Referring to FIGS. 2 and 3, slide member 350 further comprises an elongate base 352 disposed transversely to the overall fluid flow path through combination 300 from syringe barrel 405 through needle 390. Base 352 desirably comprises an opening 364 having an inside diameter that is slightly larger than the outside diameter of the substantially cylindrical portion of actuator 306 so that all but the rear portion of actuator 306 is receivable through opening 364 to facilitate rotatably mounting actuator 306 to base 352 of slide member 350. Two opposed radially projecting tabs 310 adjacent to rear opening 367 of actuator 306 are receivable through cooperatively configured arcuate recesses 366 (one of which is visible in FIG. 2) that cooperate with opening 364 to facilitate the insertion of the forwardly extending end of actuator 306 through opening 364. After tabs 310 are passed through recesses 366, actuator 306 can be rotated to a position relative to base 352 where tabs 310 are no longer aligned with recesses 366, thereby causing actuator 306 to be rotatably mounted to base 352 of slide member 350 with the forwardly facing surface of actuator disposed forwardly of base 352. Once frontal attachment 301 is fully assembled, frontal attachment 301 can be mounted to syringe 402 by aligning actuator 306 with luer lock connector 406 of syringe, inserting luer tip 404 through opening 367 in the front of actuator 306 into frictional engagement with a tapered luer receptacle formed inside the rear portion of actuator 306. As luer tip 404 is advanced through opening 367, tabs 310 can be threadedly engaged with female threads visible inside the collar portion of luer lock connector 406. As actuator 306 is threaded into luer lock connector 406, a fluid tight connection is desirably formed between actuator 306 and barrel 402.

Slide member 350 desirably further comprises an integrally formed, rearwardly projecting needle retraction chamber 308 comprising open end 362 and closed end 314 that are spaced laterally apart from opening 364. Base 352 desirably comprises a forwardly projecting base section 354, which provides dimensional relief relative to the remainder of base 352. The dimensional relief between base section 354 and base 352 is substantially equal to the thickness of arcuate rotation guide 372 disposed opposite to cam sections 373, 374 on the front face of actuator 306. This dimensional relief allows the front face of actuator 306 to be in substantially the same transverse plane as the front face of base section 354 around opening 362 of needle retraction chamber 308, which becomes significant in the context of the linear translational motion of slide member 350 relative to body 302 that occurs just prior to needle retraction. After actuator 306 has been mounted in rotatable relation to slide member 350 and after the rear end of actuator 306 has been engaged with luer lock connector 406 of syringe 402, it will also be appreciated that cam sections 373, 374 can be rotated relative to slide member 350 by rotating barrel 405 of syringe 402 relative to slide member 350.

Notch 375 is desirably provided between cam sections 373, 374 and is cooperatively aligned with notch 325 of body 302 and notch 365 of base 352 to facilitate the releasable locking of actuator 306 and slide member 350 to prevent relative motion between them that could allow accidental premature needle retraction to occur prior to use of frontal attachment if syringe 402 is inadvertently rotated relative to slide member 350. Locking rib 317 of removable needle cover 312 (visible in FIG. 3) is desirably configured to slidably engage notches 375, 325 and 365 and restrict relative rotational movement between the two notches until cover 312 is removed just prior to use of frontal attachment 301.

The retractable needle assembly of the invention preferably comprises needle 390 in combination with needle retraction mechanism 322 (FIG. 3) that further comprises needle holder 380 and spring 388. Needle 390 with forwardly facing beveled tip 392 is desirably secured in fixed relation to needle holder 380, which further comprises an elongate stem section 384 having an outside diameter slightly smaller than the inside diameter of compression spring 388, and a larger diameter head section 382 with a rear face comprising annular recess 383. The outside diameter of forwardly facing annular surface of head section 382 should be great enough to provide an engagement surface for the rearwardly facing end of spring 388 prior to and during needle retraction.

A centrally disposed, longitudinally extending fluid flow path 385 is provided through needle holder 380. It should be appreciated that compression spring 388 is depicted in FIGS. 2 and 3 in its compressed state as it would appear in the assembled frontal attachment 301 prior to retraction. When relaxed, as spring 388 would be prior to assembly of frontal attachment 301, spring 388 would appear as depicted in simplified, diagrammatic form in FIG. 7, except that it would not be disposed inside needle retraction chamber 308. It should also be appreciated that needle 390 can be attached in fixed relation to needle holder 380 by any suitable means, including for example, by gluing or press fit, or can be attached to another needle holder insert (not shown) that is, for example, threadedly engageable with the free end of stem section 384. Thus, it is possible to provide frontal attachments 301 in a variety of different needle sizes with either fixed or changeable needles.

Fluid seal receptacle 377 (FIG. 2) is also desirably provided in front face of actuator 306 to receive and seat fluid seal 378, which is preferably a substantially cylindrical elastomeric element having an axial fluid flow path 379 coaxially aligned with needle 390. The ends of fluid seal 378 are desirably chamfered or radiused to facilitate insertion into fluid seal receptacle 377 and fluid tight engagement with annulus 383 in head 382 of needle holder 380.

Body 302 of frontal attachment is desirably attachable to slide member 350 in such manner that slide member 350 can slide transversely relative to the longitudinal axis and the fluid flow path through frontal attachment 301 a distance that is sufficient to reposition needle retraction chamber 308 to achieve needle retraction following an injection. In the embodiment shown in FIGS. 2 and 3, body 302 comprises front wall 330, opposed rearwardly projecting walls 304, 307, forwardly projecting tubular nose 326 defining the front portion of stepped, interior bore 328. Annular recess 332 is desirably provided in front wall 330 to receive head section 382 of needle holder 380 when needle retraction mechanism 322 is seated inside body 302 prior to its assembly with actuator 306 and slide member 350. Two opposed snap rails 329, 331 (FIG. 9) are desirably provided as part of the body, with one of snap rails 329, 331 being disposed on the inside surface of each of rearwardly projecting walls 304, 307 of body 302 to facilitate the assembly of body 302 to slide member 350. Each of snap rails 329, 331 desirably comprises an inclined surface intersecting with a forwardly facing square shoulder that allows body 302 to be snapped into slidable engagement with slide member 350 in an axial direction, after which the only relative movement permitted between body 302 and base 352 or base section 354 of slide member 350 is sliding movement that is linear and translational in a plane transverse to the longitudinal axis through needle 390.

Figure 10:
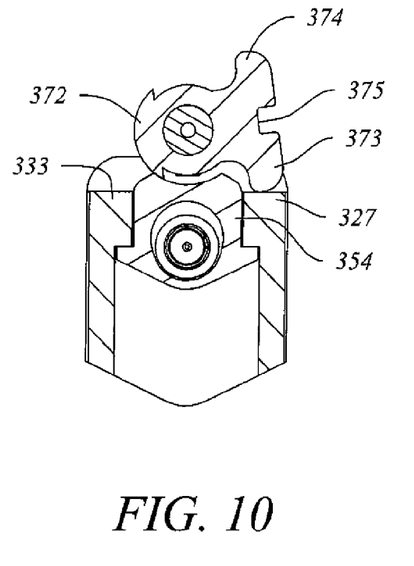
FIG. 10 is a cross-sectional view taken along line 10-10 of FIG. 6 in a plane through the cam sections that is transverse to the longitudinal axis through the combination.
Figure 11:
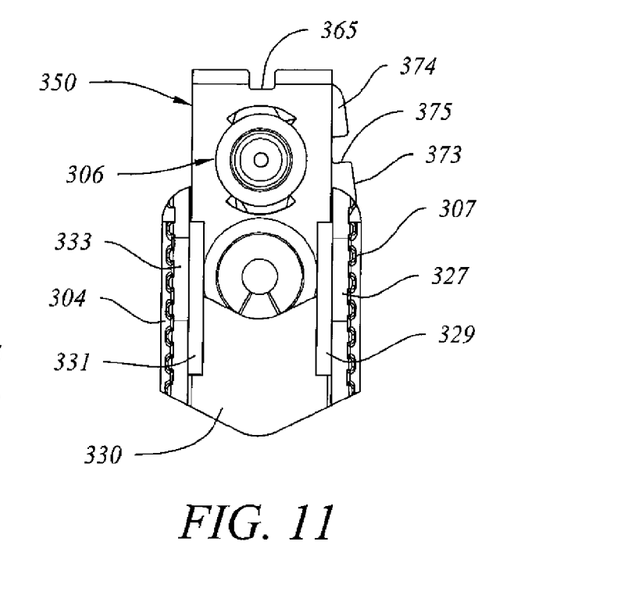
FIG. 11 is the frontal attachment of FIG. 9 with the needle cap removed, the slide member repositioned to the needle retraction position.
Figure 12:
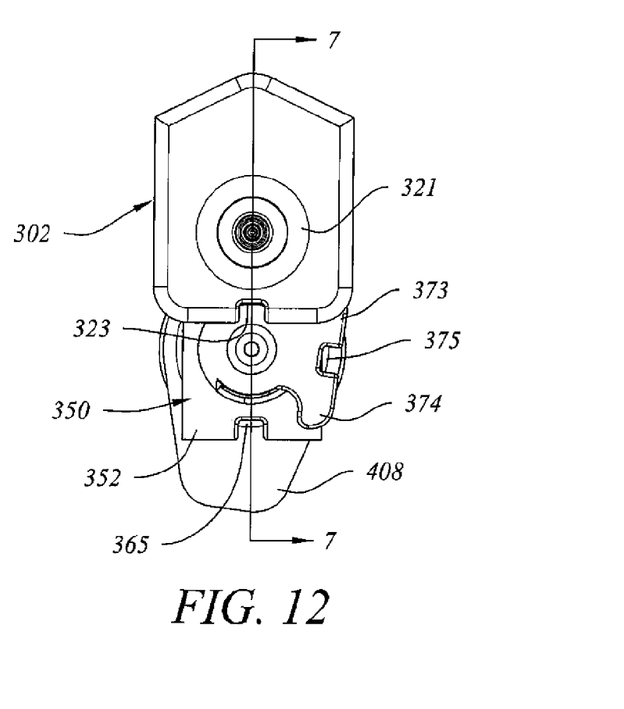
FIG. 12 is a bottom plan view of the combination of FIG. 6.

Two opposed rotation stop blocks 327, 333 (visible in FIGS. 9-11) are desirably provided in body 302 to provide engagement surfaces for cam sections 373, 374 when actuator 306 is rotated to initiate needle retraction. Each of rotation stop blocks 327, 333 is desirably disposed at the intersection of front wall 330 with the adjacent rearwardly projecting wall 307, and is offset a short distance from the edge of front wall 330 that comprises notch 325 to facilitate engagement of one of cam sections 373, 374, depending upon the direction syringe barrel 405 is rotated relative to body 302 to initiate needle retraction following an injection. In one preferred embodiment of the invention, snap rails 329, 331 and rotation stop blocks 327, 333 are integrally molded parts of body 302. Each outwardly facing surface of rearwardly projecting walls 304, 307 is desirably further provided with surface texturing or undulations to make body 302 more easily graspable by a user seeking to stabilize body 302 against accidental movement with one hand while twisting or rotating syringe 402 relative to body 302 with the other hand to initiate needle retraction.

Again referring to FIGS. 2 and 3, removable needle cover 312 desirably comprises a tubular member 313 having a forwardly facing closed end 318 and a rearwardly facing open end 316. Open end 316 is defined by a flange having tapered annular recess 319 desirably conforming to annular radius 321 at the intersection of tubular nose 326 with front wall 330 of body 302, which flange also provides support for rearwardly projecting cover release tab 305 and locking rib 317 as previously described. When removable cover 312 is in place over needle 390 and tubular nose 326 prior to use, syringe 402 cannot be rotated relative to body 302 because locking rib 317 retains positional alignment of body 302 with actuator 306 and slide member 350.

During assembly of frontal attachment 301, actuator 306 is desirably attached to slide member 350 and fluid seal 378 is inserted into fluid seal receptacle 377. According to one possible method of assembly, needle retraction mechanism 322 is assembled by sliding spring 388 onto needle holder stem section 384 and spring 388 is compressed so that retraction mechanism 322 can be seated in body 302 and held in that position while the assembled actuator 306 and slide member 350 are aligned and snapped into position relative to body 302, after which snap rails 329 hold spring 388 in compression while needle cover 312 is installed over needle 390. It should be appreciated that needle 390 can be assembled to needle holder 380 either before or after body 302 is connected to actuator 306 and slide member 350.

Figure 4:
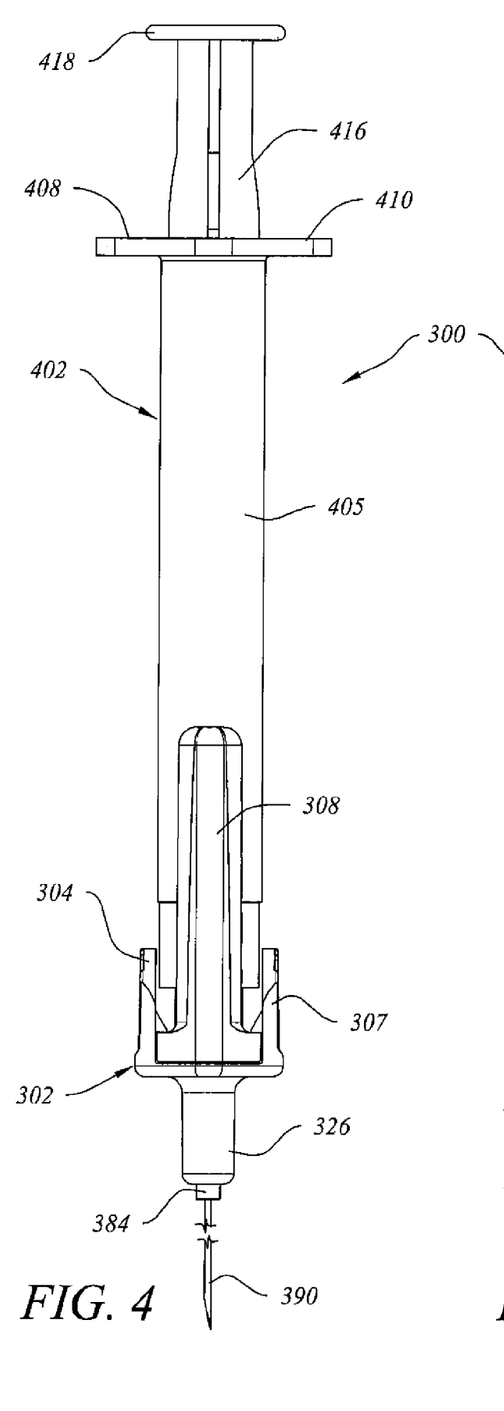
FIG. 4 is a right side elevation view of the combination of FIG. 1 with the needle cover removed to expose the forwardly projecting needle.
Figure 5:
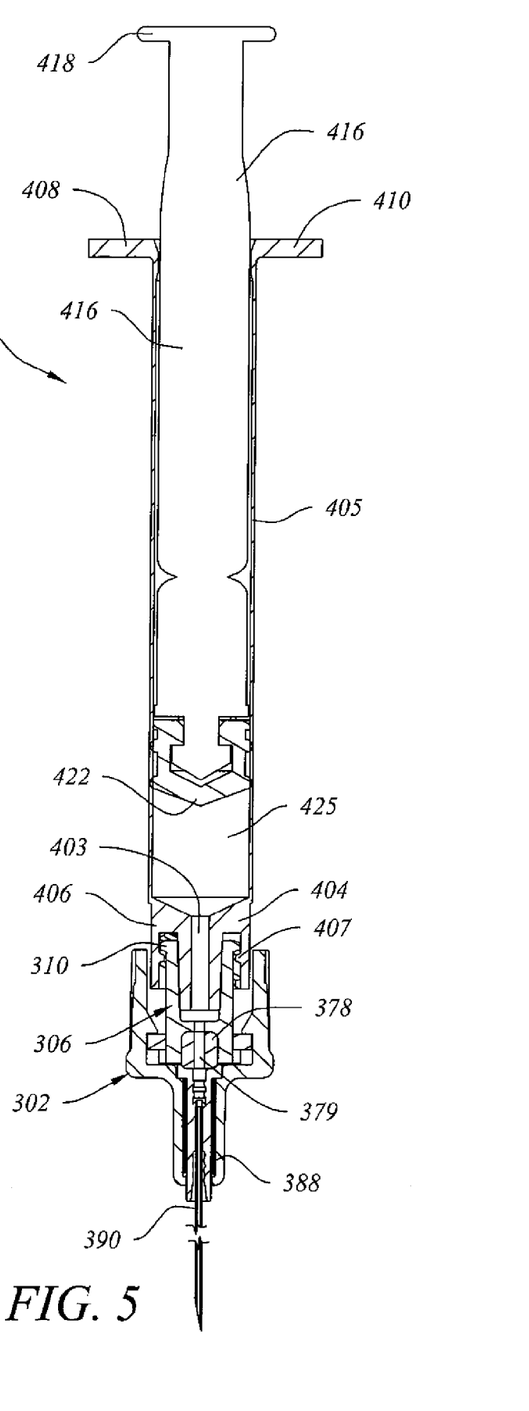
FIG. 5 is a cross-sectional view of the combination of FIG. 4 taken along line 5-5 of FIG. 8.
Figure 8:
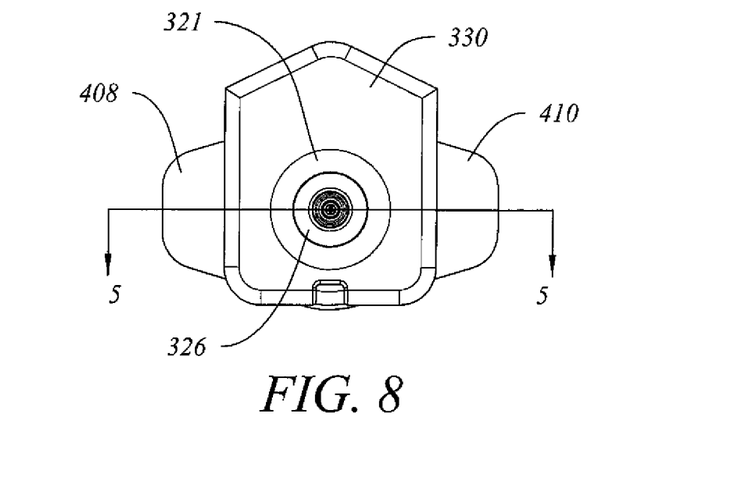
FIG. 8 is a bottom plan view of the combination of FIG. 4.
Figure 9:
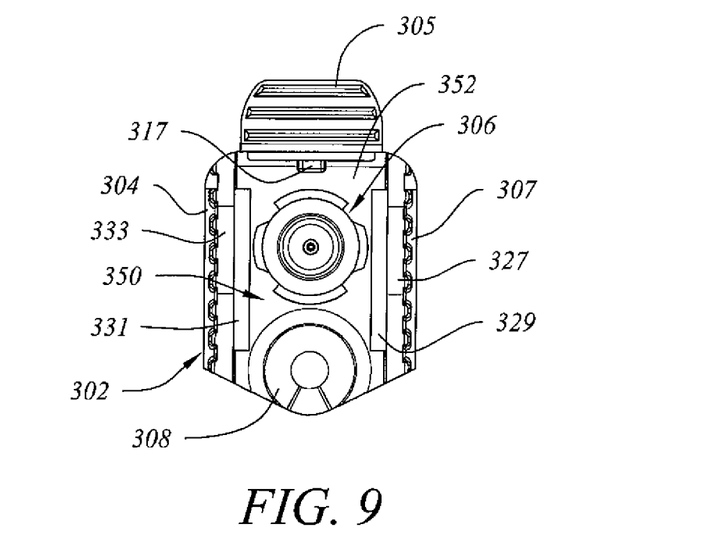
FIG. 9 is a top plan view of the frontal attachment portion of FIG. 1 oriented as in FIG. 4, but with the needle cover still attached and with the syringe broken away.

Referring to FIGS. 4, 5 and 8, combination 300 is shown with needle cover 312 removed from the position shown in FIG. 1, thereby revealing how needle 390 and the forwardly extending portion of needle holder stem section 384 desirably project forwardly of tubular nose 326 to facilitate needle attachment following assembly of the other portions of frontal attachment 301 if desired. The position of plunger handle 416 and plunger seal 422 relative to barrel 405 are consistent with what they might be either prior to or following aspiration, and prior to injection. The rotational position of barrel 405 is observed by noting the position of needle retraction chamber 308 in relation to finger grips 408, 410. FIG. 9 shows the relative positioning of cover release tab 305, locking rib 317 (engaged in notch 365 of slide member 350), actuator 306, slide member 350, needle retraction chamber 308 and body 302 (including rearwardly projecting walls 304, 307 and snap rails 329, 331) of the assembled frontal attachment with the needle cover still in place. FIG. 5 shows the relative positioning of the component parts of the assembled frontal attachment 301 with cover 312 removed, and shows internal space 425 ahead of plunger seal 422 that is the fluid chamber of syringe 402 if fluid has been aspirated into syringe 402 in preparation for an injection.

Figure 6:
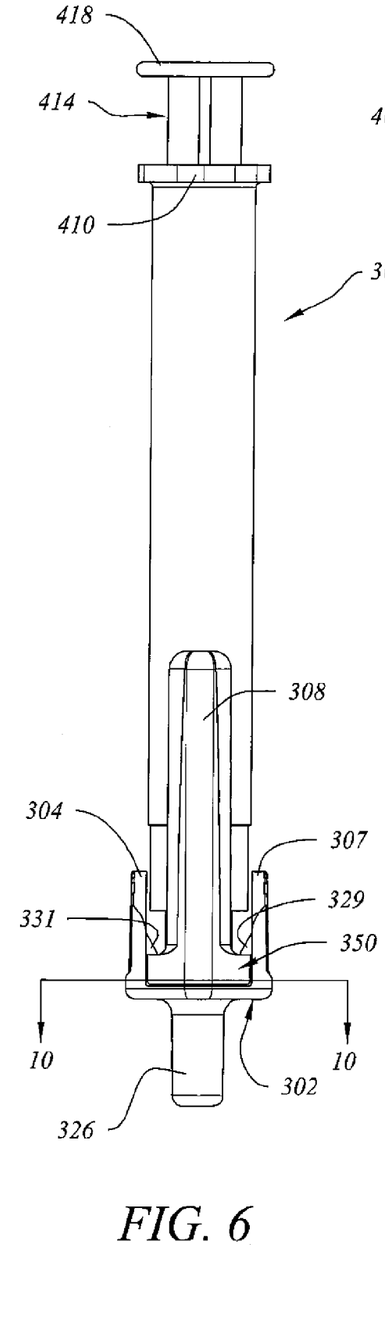
FIG. 6 is a right side elevation view of the combination of FIG. 4 following needle retraction, with the plunger handle fully depressed inside the syringe barrel, the syringe barrel rotated 90° relative to the frontal attachment, and the needle retracted.
Figure 7:
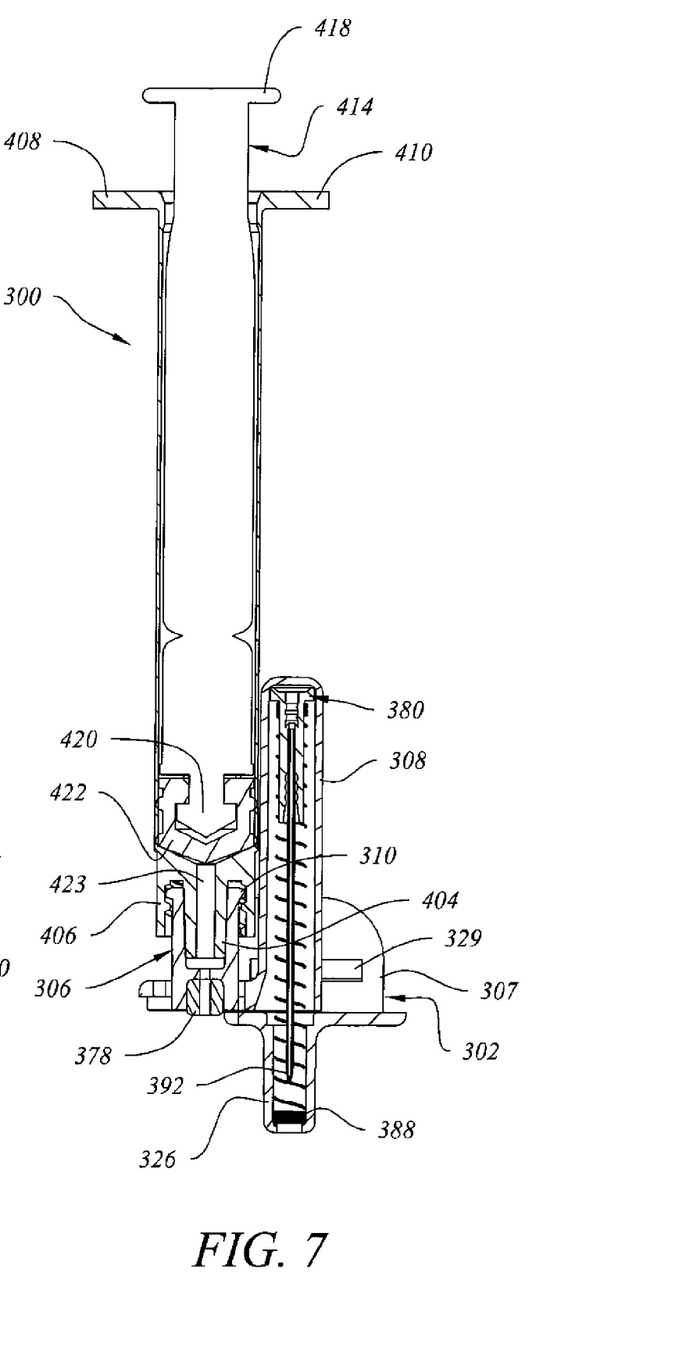
FIG. 7 is a cross-sectional front elevation view of the combination of FIG. 6, taken along line 7-7 of FIG. 12.

Referring to FIGS. 6-7, plunger assembly 414 is fully depressed inside the syringe barrel, in the position that it would be following an injection and retraction of the needle into needle retraction chamber 308. FIG. 7 shows that the retraction process has repositioned needle retraction chamber 308 over tubular nose 326, thereby allowing spring 388 to force needle holder 380 upwardly into needle retraction chamber 308 a sufficient distance that needle tip 392 no longer projects forwardly of tubular nose 326, thereby rendering combination 301 "safe."

The method by which needle retraction is achieved through use of frontal attachment 301 is further described with reference to FIGS. 7, 10-12. Following an injection, needle retraction is initiated when the syringe user grasps rearwardly projecting walls 304, 307 of body 302 to stabilize body 302 during retraction, and with the other hand rotates the syringe in either direction relative to body 302. As the syringe is rotated, actuator 306 is also rotated relative to body 302, causing rotation guide 372 to slide along the facing surface of a cooperatively configured arcuate recess on the cam-facing side of base section 354 until one of cam members 373, 374 engages and is stopped by one of rotation stop blocks 327, 333. Cam members 373, 374 are preferably configured so that one of them (depending upon the direction of rotation) will initially contact one of the two rotation stop blocks 327, 333. Another function of rotation stop blocks 327, 333 is to limit the travel of slide member 350 relative to body 302.

When one of cam members 373, 374 initially contacts one of rotational stop blocks 327, 333, slide member 350 and needle retraction chamber 308 begin sliding transversely relative to body 302 and needle holder 380, causing fluid seal 378 to disengage from needle holder 380. As actuator 306 continues to rotate relative to slide member 350 in response to rotation of the syringe attached to actuator 306, the engaged cam member (in this case 373) continues to move slide member 350 transversely and the forwardly facing surfaces of actuator 306 and surface section 354 (which are desirably substantially coplanar) directly engage needle holder 380 and continue to hold spring 388 in compression until the linear translational movement of slide member 350 relative to body 302 causes needle retraction chamber 308 to become sufficiently aligned with needle holder 380 that compressed spring 388 causes needle holder 380 to move rearwardly into needle retraction chamber 308, which also carries needle tip 392 rearwardly into tubular nose 326 of body 302 as seen in FIG. 7. Retraction spring 388 is desirably designed and configured to exert sufficient force to fully retract needle tip 392 from a patient's body into body 302. After spring 388 expands to the position shown in FIG. 7, any further translational motion of slide member 350 relative to body 302 is impeded by relaxed spring 388, and combination 300 is rendered "safe" because needle tip 392 is contained within body 302 and frontal attachment 301 cannot be reused.

Although other similarly effective materials can be used, body 302, actuator 306, slide member 350, needle holder 380 and cover 312 are all desirably molded from one or more suitable moldable polymeric materials suitable for use in medical devices of this type. Such materials and molding methods are believed to be well known to those of ordinary skill in the art. Similarly, it will be appreciated by those of skill in the art of syringe design and manufacture that a medical device such as frontal attachment 301 disclosed here can be used with syringes that either pre-filled or not, and that may comprise component parts made of glass or other materials more suitable for particular fluids and applications. It will also be appreciated that fluid seal 378 is desirably made of a rubbery or elastomeric polymeric material of the types commonly known for use in such medical applications. As such, materials used in the fabrication of this and other medical devices must be approved by the relevant regulatory authorities for use in such devices. Retraction spring 388 and needle 390 are desirably made of stainless steel or any other similarly effective material approved for such uses.

While an apparatus and method of the invention are primarily described here in relation to one embodiment that is a frontal attachment to a syringe having a luer lock connector, it will become apparent to those of ordinary skill in the art upon reading the subject disclosure in relation to the drawings that the subject needle retraction apparatus is likewise applicable to catheters, blood collection sets and other fluid infusion and collection devices. The subject invention is useful with devices having glass or plastic components and can be configured as an attachment to an existing medical device, can be assembled as part of a medical device during manufacture, or portions of the device (such as, for example, the actuator) can be integrally molded together with another device such as a syringe barrel. It will also be appreciated that other cam configurations and locking structures that are similarly effective can be substituted for the particular configurations disclosed here within the scope of the invention.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventors are legally entitled.

We claim:

1. A needle retraction apparatus for use with medical devices, said medical devices including liquid infusion devices and liquid collection devices, the apparatus comprising:
    a body;
    a retractable needle assembly further comprising a needle projecting forwardly from the body;
    a slide member supported by the body, the slide member further comprising a rearwardly projecting needle retraction chamber; and
    an actuator rotatably supported by and connected to the slide member, the actuator further comprising a connector member providing fluid communication with the liquid infusion device or liquid collection device;
    wherein the body is attachable to the slide member so that relative movement between the body and slide member is limited to sliding movement that is linear and translation in a plane transverse to a longitude axis through the needle; and
    wherein rotation of the actuator relative to the slide member initiates needle retraction by causing the needle retraction chamber to slide transversely into alignment with the needle.

2. The needle retraction apparatus of claim 1 configured as a frontal attachment to the liquid infusion device or liquid collection device.

3. The needle retraction apparatus of claim 2 wherein the liquid infusion device or liquid collection device is a syringe.

4. The needle retraction apparatus of claim 3 wherein the connector member is configured to form a luer lock connection with the syringe.

5. The needle retraction apparatus of claim 1 wherein the body further comprises first and second rearwardly projecting walls.

6. The needle retraction apparatus of claim 5 wherein the rearwardly projecting walls further comprise gripping surfaces.

7. The needle retraction apparatus of claim 5 wherein each rearwardly projecting wall further comprises a snap rail.

8. The needle retraction apparatus of claim 5 wherein each rearwardly projecting wall further comprises a rotation stop block.

9. The needle retraction apparatus of claim 8 wherein each rotation stop block limits linear movement of the slide member relative to the body.

10. The needle retraction apparatus of claim 1 wherein the body further comprises a forwardly projecting tubular nose.

11. The needle retraction apparatus of claim 1 wherein the body further comprises a rearwardly facing annular recess.

12. The needle retraction apparatus of claim 1 wherein the body, slide member and actuator each further comprises a notch, and wherein all three notches are alignable.

13. The needle retraction apparatus of claim 1 wherein the retractable needle assembly further comprises a needle holder and a compressible spring that biases the needle rearwardly relative to the body.

14. The needle retraction apparatus of claim 13 wherein the compressible spring has a spring force sufficient to retract the needle from a patient.

15. The needle retraction apparatus of claim 1 wherein the body and slide member are cooperatively configured to allow the slide member to move transversely relative to a longitudinal axis through the needle.

16. The needle retraction apparatus of claim 1 wherein the slide member further comprises a first opening through which the actuator is receivable and attachable to the slide member.

17. The needle retraction apparatus of claim 1 wherein the actuator further comprises at least one cam member that is rotatable relative to the slide member and the body.

18. The needle retraction apparatus of claim 17 wherein rotation of the actuator relative to the slide member causes the at least one cam member to engage the body and cause relative linear translational movement between the body and the slide member until the needle retraction chamber is substantially coaxially aligned with the needle retraction assembly.

19. The needle retraction apparatus of claim 17 wherein the actuator comprises two laterally spaced cam members.

20. The needle retraction apparatus of claim 19 wherein a notch is disposed between the two laterally spaced cam members.

21. The needle retraction apparatus of claim 1 wherein the slide member comprises a stepped forwardly facing surface.

22. The needle retraction apparatus of claim 16 wherein the slide member further comprises a second opening into the needle retraction chamber.

23. The needle retraction apparatus of claim 22 wherein the first and second openings in the slide member are laterally spaced apart.

24. The needle retraction apparatus of claim 1 in combination with a syringe having a luer lock connector comprising a forwardly projecting luer tip cooperatively configured with the luer receptacle of the actuator and a female thread cooperatively configured with the projecting tabs of the actuator.

25. The needle retraction apparatus of claim 1, further comprising a removable needle cover.

26. The needle retraction apparatus of claim 12, further comprising a removable needle cover.

27. The needle retraction apparatus of claim 26 wherein the removable needle cover further comprises a locking rib that is releasably engageable with the aligned notches of the body, slide member and actuator.

28. The needle retraction apparatus of claim 27 wherein the locking rib prevents relative rotational movement among the body, slide member and actuator until the needle cover is removed from the apparatus.

* * * * *

UNITED STATES PATENT AND TRADEMARK OFFICE
CERTIFICATE OF CORRECTION

PATENT NO. : 9,138,545 B2  
APPLICATION NO. : 13/714819  
DATED : September 22, 2015  
INVENTOR(S) : Thomas J. Shaw et al.

Page 1 of 1

It is certified that error appears in the above-identified patent and that said Letters Patent is hereby corrected as shown below:

Claims
Column 10, ln. 13, claim 1 "translation" should read --translational--.

Signed and Sealed this
Second Day of August, 2016

Michelle K. Lee
*Director of the United States Patent and Trademark Office*

UNITED STATES PATENT AND TRADEMARK OFFICE
CERTIFICATE OF CORRECTION

PATENT NO. : 9,138,545 B2
APPLICATION NO. : 13/714819
DATED : September 22, 2015
INVENTOR(S) : Thomas J. Shaw et al.

It is certified that error appears in the above-identified patent and that said Letters Patent is hereby corrected as shown below:

In the Claims

Column 10, Line 14, "longitude" should read --longitudinal--.

Column 11, Line 4, "needle retraction assembly" should read --retractable needle assembly--.

Signed and Sealed this
Twentieth Day of August, 2019

Andrei Iancu
*Director of the United States Patent and Trademark Office*